United States Patent [19]

Baumoel

[11] Patent Number: 5,271,267
[45] Date of Patent: Dec. 21, 1993

[54] METHOD AND APPARATUS FOR DETERMINING FLUID PROPERTIES FROM SONIC/TEMPERATURE FLUID SIGNATURE

[76] Inventor: Joseph Baumoel, 155 Plant Ave., Hauppauge, N.Y. 11788

[21] Appl. No.: 848,266

[22] Filed: Mar. 9, 1992

[51] Int. Cl.⁵ ............................ G01N 11/00; G01N 9/24
[52] U.S. Cl. ................................... 73/54.41; 73/32 A
[58] Field of Search ............... 73/54.41, 32 A, 597, 73/54.02

[56] References Cited

U.S. PATENT DOCUMENTS

| | | | |
|---|---|---|---|
| 4,235,099 | 11/1980 | Ishizaka | 73/32 A |
| 4,331,025 | 5/1982 | Ord, Jr. | 73/54.41 X |
| 4,522,068 | 6/1985 | Smith | 73/32 A |
| 4,559,810 | 12/1985 | Hinrichs et al. | 73/54.41 |
| 4,934,177 | 6/1990 | Cuthbertson et al. | 73/32 A |

FOREIGN PATENT DOCUMENTS

| | | | |
|---|---|---|---|
| 241956 | 1/1987 | German Democratic Rep. | 73/32 A |
| 2543 | 1/1991 | Japan | 73/54.41 |
| 88/08516 | 11/1988 | World Int. Prop. O. | 73/32 A |

*Primary Examiner*—Tom Noland
*Assistant Examiner*—Joseph W. Roskos
*Attorney, Agent, or Firm*—Ostrolenk, Faber, Gerb & Soffen

[57] ABSTRACT

A method and apparatus for non-intrusively identifying a property of a fluid in a container or pipe. The method includes propagating, from a transmitter, sonic energy into the fluid in the container; receiving the sonic energy at a reception site after a defined time delay determined by the nature of the fluid in the container; determining the time for the sonic energy to propagate from the transmitter to the reception site; determining the sonic propagation velocity of the sonic energy in the fluid from the determined time and from knowledge of the distance from the transmitter to reception site; determining the temperature of the fluid in the container; and determining the fluid property from the relationship between the sonic propagation velocity in the fluid and temperature. The properties determined may include viscosity and density, and if the fluid is known, pressure. Additionally, if the fluid is unknown, but known to be one of a number of fluids, the identity of the fluid can also be determined.

14 Claims, 3 Drawing Sheets

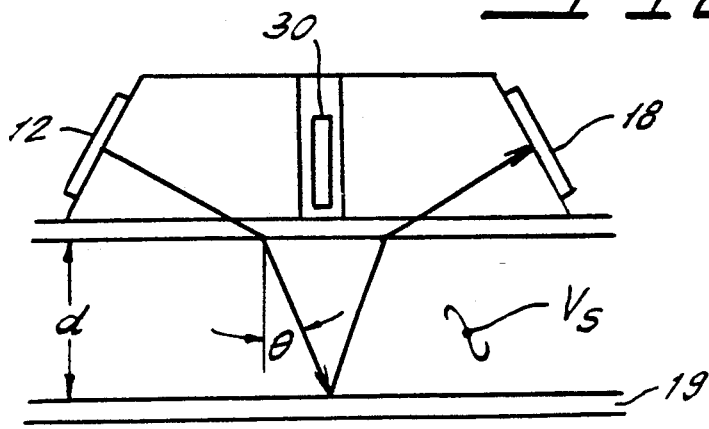
FIG. 1A
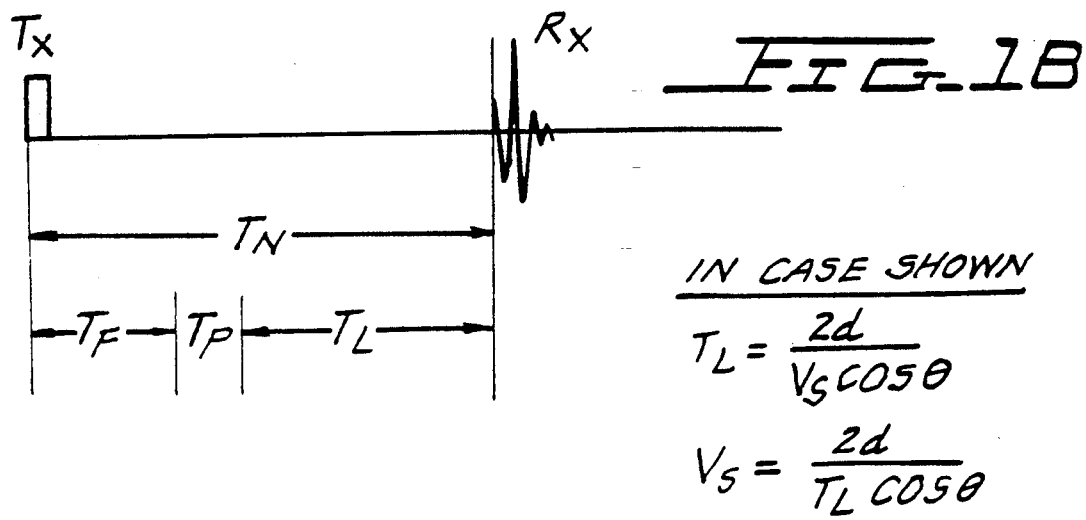
FIG. 1B
IN CASE SHOWN
$$T_L = \frac{2d}{V_S \cos\theta}$$
$$V_S = \frac{2d}{T_L \cos\theta}$$
FIG. 5
| MEASURED $V_S$ AT 70° | $V_S$ AT 60° | PROP AT 60° | PROP AT 70° | FIG 3,4 CURVE |
|---|---|---|---|---|
| 1245 | 1300 | 30 | 40 | X |
| 1375 | 1450 | 40 | 50 | Y |
| 1525 | 1650 | 50 | 60 | Z |
| 1640 | 1800 | 60 | 70 | W |

METHOD AND APPARATUS FOR DETERMINING FLUID PROPERTIES FROM SONIC/TEMPERATURE FLUID SIGNATURE

BACKGROUND OF THE INVENTION

The present invention relates to a method and apparatus for determining the properties of a fluid traversing through a container or pipe. More particularly, the present invention relates to such a method and apparatus for non-invasively determining such fluid properties as density and viscosity using sonic energy propagated into the fluid to determine sonic propagation velocity of the sonic energy in the fluid in the container or pipe. The determined sonic propagation velocity can then be used as a "signature" along with fluid temperature to determine the fluid properties such as density and viscosity. Additionally, if the fluid identity is known, the pressure can also be determined. Furthermore, if the user has advance knowledge of the types of fluids conveyed in the pipeline, the fluid identity from amongst the possible fluids carried in the pipeline may be determined.

Systems are known which utilize the propagation of sonic energy through a container containing a fluid medium in order to determine the pressure of the fluid medium. For example, U.S. Pat. No. 3,977,252 to Krilova discloses a system for measuring liquid pressure in pipelines. This system is contactless and sends an ultrasonic pulse through the liquid, determines the rate of propagation of the pulse through the liquid and then determines the pressure of the liquid as a function of the propagation rate.

U.S. Pat. No. 3,942,381 to Brown discloses a clamp-on type transducer for measuring the time taken for an echo to travel through a pressurized bottle and for thereby determining the pressure of gas within the bottle.

U.S. Pat. No. 3,859,846 to Asada discloses a system with ultrasonic wave transmitting and receiving elements for locating an interface between different liquids flowing through a pipeline.

To applicant's knowledge, there is not, however, a system for determining the properties of a fluid present in a container, for example, the density and viscosity of a fluid in a pipeline, based upon non-invasive determination of sonic propagation velocity and fluid temperature, or which allows the determination, based upon advance knowledge of the types of fluids carried by the pipeline, of the fluid type from amongst several types. Furthermore, the invention provides a method based upon a knowledge of the fluid type, of determining the pressure of the fluid.

SUMMARY OF THE INVENTION

It is an object of the present invention to provide a method and apparatus for determining the properties of a fluid in a container or pipeline in a non-intrusive manner.

It is yet still a further object of the present invention to provide such a non-intrusive method and apparatus for determining the properties of a fluid in a pipeline using ultrasonic techniques.

It is yet still a further object of the present invention to provide such a method and apparatus for determining the properties of a fluid in a pipeline from a knowledge of the fluid temperature and sonic propagation velocity of sonic energy in the fluid.

In particular, it is an object of the invention to provide a method and apparatus for determining properties of the fluid such as density and viscosity.

In addition, it is also an object of the invention to provide a method and apparatus which, based on the determination of the particular fluid properties, allows identification of the fluid type if some knowledge exists of the fluid types from amongst a number of fluid types carried in the pipeline.

It is yet still a further object of the invention to determine the fluid pressure, once the fluid type is identified, or if the fluid type is known.

The above and other objects of the present invention are achieved by a method for determining a property of a fluid in a container comprising the steps of propagating from a transmitter sonic energy into the fluid in the container; receiving the sonic energy at a reception site after a defined time delay determined by the nature of the fluid in the container; determining the time for the sonic energy to propagate from the transmitter to the reception site; determining the sonic velocity of the sonic energy from the determined time and from knowledge of the distance from transmitter to reception site; determining the temperature of the fluid in the container; and determining the fluid property from the relationship between the sonic propagation velocity in the fluid and temperature.

Other features and advantages of the present invention will become apparent from the following detailed description of the invention.

BRIEF DESCRIPTION OF THE DRAWINGS

The invention will be described in greater detail in the following detailed description with reference to the drawings in which:

FIG. 1A shows one arrangement of transducers for transmitting sonic energy into a fluid-carrying container and for receiving the energy after a predetermined time depending on the fluid identity;

FIG. 1B shows signals and time periods in the diagram of FIG. 1A;

FIG. 5 shows an exemplary table for determining fluid properties based on the calculated sonic propagation velocity related to a standard temperature using a temperature coefficient.

DETAILED DESCRIPTION OF THE DRAWINGS

It has been discovered that liquids, at least many petroleum products, have a characteristic "signature" in terms of their sonic propagation velocity ($V_s$) versus temperature characteristic. In addition, they appear to have a characteristic "family" temperature coefficient. This means that a liquid's properties, and possibly its identification, can be determined by its $V_s$ at some reference temperature, say 60° fahrenheit. This information, together with the temperature coefficient, is sufficient to identify the liquid properties if its temperature coefficient is constant over the temperature range, as appears to be the case for most liquids. Alternatively, a family of curves can be generated, thereby taking into account nonlinearities, and from these families of curves relating temperature and sonic propagation velocity for particular liquids, once the temperature and sonic propagation velocity are determined, the liquid properties can be found by determining which curve the measured variables intersect. These properties include density and viscosity, and if the liquid type is known, pressure. In the case where the temperature coefficient is known to be linear, although it need not be, a measure of $V_s$ at any temperature can be related back to a standard temperature, for example 60° fahrenheit, and thus the properties of the liquid can be determined based on the calculated value of $V_s$ at the standard temperature. The properties of mixture of liquids may be determined by an interpolation technique, to be described below.

FIG. 1A shows a typical arrangement of the transducers in accordance with a system implementing the invention. A first transducer 12 transmits sonic energy into a pipeline 19. The energy travels through the walls at a first refraction angle, as known to those of skill in the art. The energy travels into the fluid in the pipeline with a sonic propagation velocity $V_s$, at a second refraction angle $\Theta$. The sonic energy is reflected off the pipeline far wall and returned to a receiving transducer 18. The pipeline has a diameter d. A temperature sensor 30 is disposed on the pipeline 19 as shown.

Alternatively, as described below, transducer 18 may be disposed on the other side of the pipeline, as known to those of skill in the art, so that a reflection off the other side is not necessary.

FIG. 1B shows the relationship between the transmitted pulse $T_X$ and the received pulse $R_X$. The total transit time $T_N$ = time $T_L$ (time in liquid) + time $T_F$ (fixed delays) + time $T_P$ (time in pipe and transducer housings). The time $T_L = S/V$, where $S$ = distance =

$$\frac{2d}{\cos \theta}$$

and $V = V_S$. Therefore, $$T_L = \frac{2d}{V_s \cos \theta}.$$

or $$V_S = \frac{2d}{T_L \cos \theta}.$$

$\Theta$, the angle of refraction, can be determined from Snell's Law, allowing determination of $V_S$.

Figure 2:
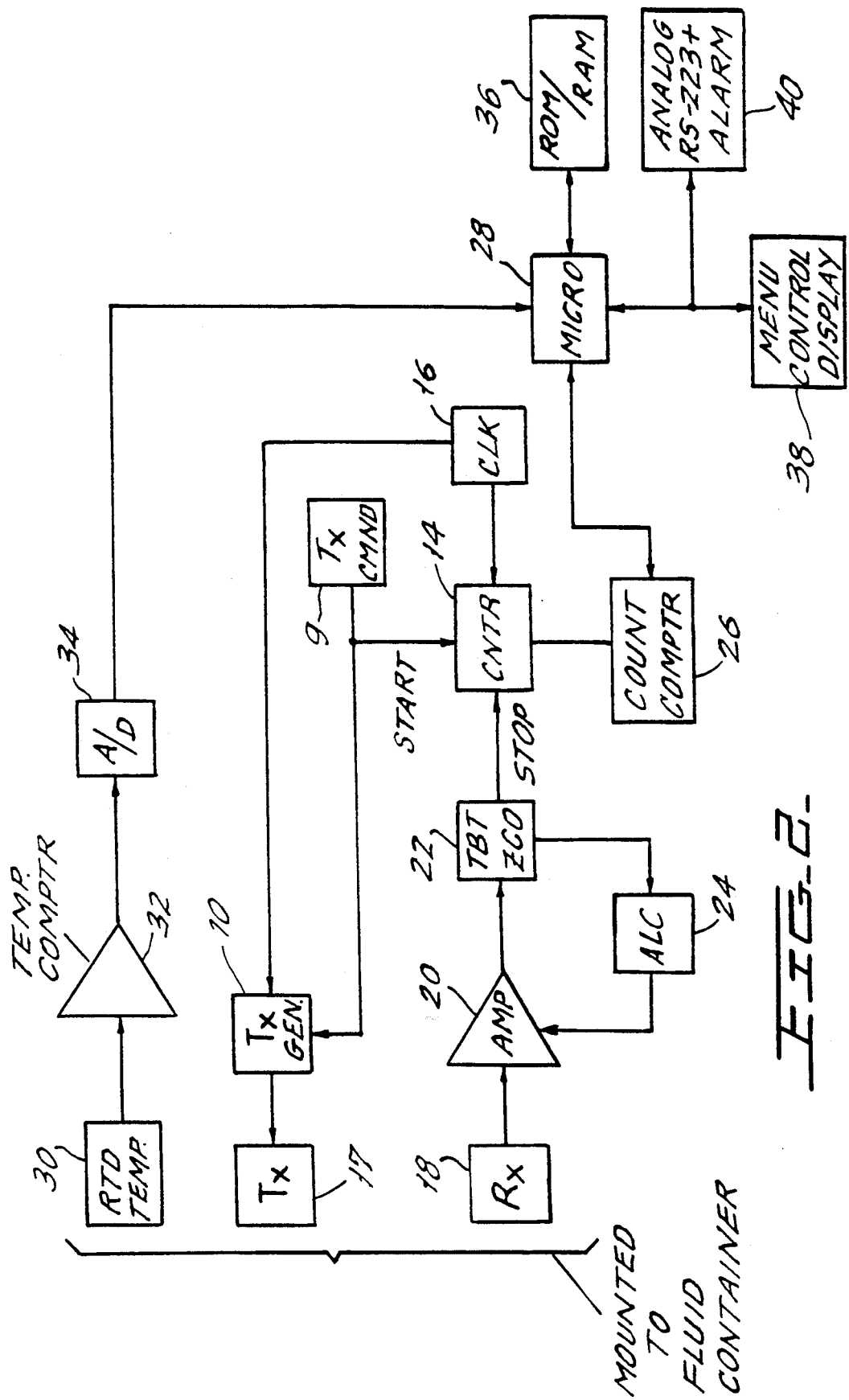
FIG. 2 shows the block diagram of a system for implementing the present invention.

FIG. 2 shows the basic block diagram of a system in accordance with the present invention. This system determines the sonic propagation velocity of the sonic energy through a liquid. The transmitting and receiving transducers 12 and 18 are coupled into the circuit of FIG. 2 as shown. As shown in FIG. 1A, the transmitting and receiving transducers may be disposed on the same side of a pipeline, but it is also possible to dispose the transducers on opposite sides of the pipeline, as shown, for example, in commonly owned U.S. Pat. No. 4,232,548.

The system shown in FIG. 2 measures the transit time and accounts for the time for transmission of the sonic energy in nonliquid paths, e.g., within the pipe or within the mounting structure for the transducers, so as to be able to calculate directly the sonic velocity $V_s$.

The benefits of attaining information on the properties of the liquid, e.g., of such parameters as pressure, density and viscosity of a liquid inside a pipe or vessel, by means of nonintrusive detection, as opposed to traditional means of intrusive detection, are obvious. They include the saving of cost of installation, increased safety against leaks or blowouts, increased reliability, freedom from need of recalibration due to wear of intrusive transducers, excellent accuracy and repeatability. In addition, the use of clamp-on technology permits taking measurements at points which do not warrant the cost of a permanent installation.

Turning again to FIGS. 1A, 1B and 2, in an embodiment of the invention, a transmit pulse is generated by a transmitter generator 10 initiated by a transmit command 9 and transmitted to the transmitting transducer 12. At the same time that the transmit command is generated, a counter 14 is started. The counter 14 collects the counts generated by a high frequency oscillator 16. The value of the counter when the sonic signal is received is a measure of the total time, $T_N$, of the pulse through the liquid plus the transducer structures and pipe 19. The sonic pulse is received by the receive transducer 18 and is provided to an amplifier 20. The receive transducer is located in a position to receive the transmitted energy after it has passed through the liquid and been affected by its temperature and internal properties, e.g., density, viscosity and pressure. The location accommodates the intended sonic path, whether direct or reflected, and whether it is subjected to refraction or not.

The counter 14 is preferably designed to count at a 35 Mhz rate, and is started at the time of transmission, and stopped by arrival of the detected, received signal. The received signal, after amplification by amplifier 20, is provided to a detector 22. The received signal can be detected by suitable zero crossover and comparator circuitry having a reference level. In the embodiment shown, when a transmitted pulse is received by receiving transducer 18, it is amplified by the amplifier 20 and gain controlled by AGC stage 24 so as to produce a fixed and predetermined peak amplitude. The detector 22 may include a comparator, with the comparator producing a pulse when the reference level of the comparator has been exceeded. The pulse from the detector stops the counter 14 and the counter value is directly related to the travel time of the sonic pulse from transmitter to receiver. This count is fed to a count comparator 26 to be compared to one or more preset count values. By comparing the count value to the preset count values, the total travel time $T_N$ can be determined. By subtraction of fixed delays due to transmission through the pipe and the transducer mounting structure and other fixed delays, such as electronic delays, well known in the art, the travel time in the liquid can be determined. See FIG. 1B. Because the distance that the sonic pulse travels through the liquid is known, the velocity can be determined as S/TL, where S = the distance traveled in the liquid and TL = the time for the sonic pulse to travel through the liquid. With reference to FIG. 1B, where the sonic pulse travels through the liquid at a refraction angle $\Theta$, determined by Snell's Law, $V_s$ is equal to 2d/TL Cos $\Theta$.

Now that the sonic velocity $V_s$ has been determined, a microcomputer 28 uses the calculated value of $V_s$, as well as the measured temperature from a temperature sensor 30. The measured temperature value is provided to an analog temperature computer 32 which converts the sensor 30 value (e.g., a resistance) to an analog voltage. The analog voltage is fed to an analog to digital converter 34, which converts the analog value into a digital signal. Computer 28 determines the fluid properties based upon the determined sonic propagation velocity and a stored temperature coefficient (i.e., an equation) or from a family of curves relating temperature and sonic propagation velocity, stored in digital memory 36. The properties of the liquid, i.e., its density and viscosity and, if determinable from knowledge of the types of fluid carried by the pipeline, the fluid identity and/or its pressure, are then displayed on a display device 38. A communications port 40 may be provided for transmission of data to other data receiving devices, and an alarm can be provided in the event of an extreme condition, e.g., high temperature, pressure, etc., to be discussed below.

Figure 3:
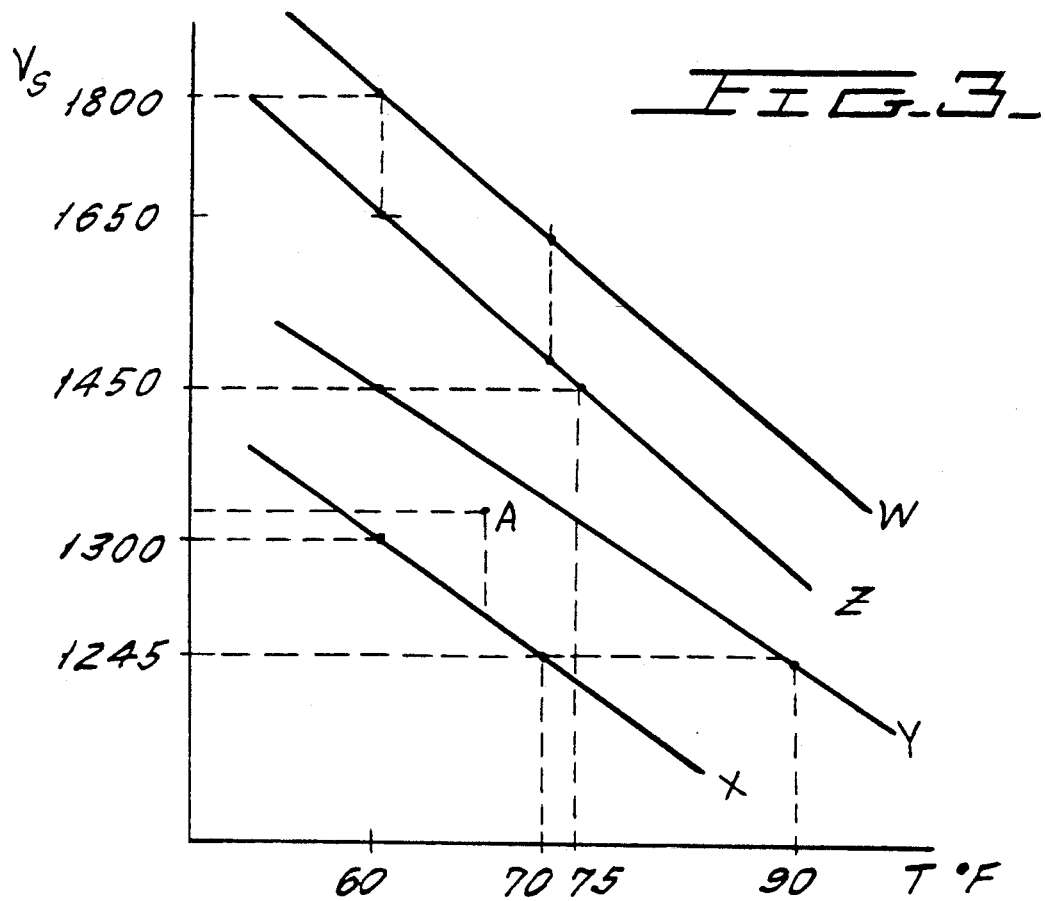
FIG. 3 is a graph showing how once the temperature and sonic propagation velocity of the fluid are determined, a general relationship between temperature and sonic propagation velocity is defined.

With reference to FIG. 3, a graph showing first characteristic curves X, Y, Z and W relating sonic propagation velocity $V_s$ and temperature is shown. These graphs can be stored in digital form as a look-up table in memory 36. Once the time TL has been determined, the value of $V_s$ has been calculated, and the temperature from sensor 30 is known, the point on one of the curves X, Y, Z and W is determined which is closest to the unique point determined by $V_s$ and T. Thus, for example, if $V_s$ is calculated to be 1245 M/S at a temperature of 70° F. it is determined that the fluid has the characteristic X. If, for example, $V_S = 1245$ M/S at a temperature of 90° F., the fluid has characteristic Y. As another example, a value of 1450 M/S calculated for $V_s$ at a temperature of 75° F. means the fluid has characteristic Z.

If the user has some knowledge of the types of fluid carried in the pipeline from amongst a plurality of fluids carried by the pipeline, the characteristic curve identified may also uniquely specify the particular fluid. Thus, the fluid type, from amongst the plurality of fluid types, can be identified. It is not always possible to identify the fluid type if one does not have knowledge of the types of fluid carried by the pipeline. For example, even though the temperature/sonic propagation velocity measures fall on curve Y, it is still possible that the fluid might be a mixture of a fluid with characteristic X and a fluid with characteristic Z, or W, for that matter. Should the intersection point of temperature and sonic propagation velocity not fall on a curve, e.g., point A in FIG. 3, an interpolation procedure can be used to determine the mixture's properties, as explained below.

Figure 4:
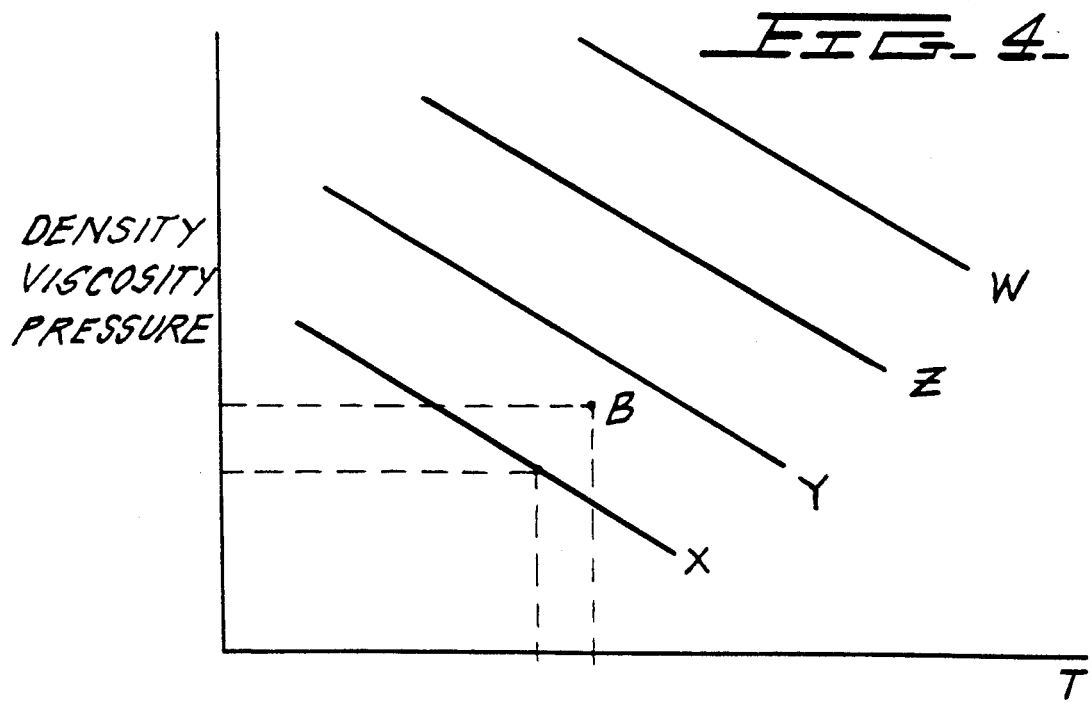
FIG. 4 shows how once the general relationship of FIG. 3 is defined, properties of the liquid, such as its density and viscosity, and if the liquid type is known, its pressure, can be determined.

Once the fluid's general characteristic has been determined (FIG. 3), using another set of characteristic curves stored in memory 36 and related to the curves of FIG. 3, the fluid properties such as density and viscosity can be displayed on the display device 38, in user selected units. The pressure of the fluid can also be determined and displayed if the fluid type is known. This is shown in FIG. 4. Should a dangerous pressure be determined, the alarm 40 can be sounded.

FIG. 4 also shows that an interpolation technique can be used to determine the fluid properties of a fluid which does not fall on one of the characteristic curves of FIG. 3. See, e.g., point A in FIG. 3 which corresponds to point B in FIG. 4.

Alternatively, if the temperature coefficient is known, the velocity calculation for a measured temperature can be related to a standard temperature, e.g., 60° F., and the liquid properties identified based on the $V_s$ value stored in a table which is closest to the temperature compensated $V_s$ value calculated using the temperature coefficient. FIG. 5 shows an example of such a table wherein the measured $V_s$ value is shown in the left column, and the compensated sonic propagation velocity at a standard temperature of 60° F., shown in the second column from the left, is used to determine the fluid characteristic. Once the fluid characteristic is known, e.g., curve X, Y, Z or W, a look-up table having the data in FIG. 4, or a suitable equation using the temperature coefficient to relate the particular fluid property, e.g., density or viscosity, to temperature, can be used to determine that property. For example, as shown in the third column from the left, the particular fluid property at 60° F., the standard temperature, can be determined once $V_s$ at the standard temperature is known. A temperature coefficient can then be used to relate the property at the standard temperature to the actual temperature (fourth column from left). The numbers and letters in FIG. 5 are directly related to the graphs show in FIG. 3, as should be clear from a comparison of the two charts.

Although the present invention has been described in relation to particular embodiments thereof, many other variations, modifications and other uses will become apparent to those skilled in the art. Therefore, the present invention should be limited not by the specific disclosure herein, but only by the appended claims.

I claim:

1. A method for determining a property of a fluid in a container, the property comprising the density or viscosity of the fluid, the method comprising:

propagating from a transmitter sonic energy into said fluid in the container;

receiving the sonic energy at a reception site after a defined time delay determined by the nature of the fluid in the container;

determining the time for the sonic energy to propagate from the transmitter to the reception site;

determining the sonic propagation velocity of the sonic energy in the fluid from the determined time and from knowledge of the distance from the transmitter to reception site;

determining the temperature of the fluid in the container; and determining the fluid property from the relationship between the sonic propagation velocity in the fluid and temperature.

2. The method recited in claim 1, wherein the step of determining the fluid property further comprises determining the pressure of the fluid in the container.

3. The method recited in claim 1, wherein the step of determining the fluid property comprises storing, in a look-up table, a plurality of first characteristic curves relating temperature and fluid sonic propagation velocity and a plurality of second characteristic curves each associated with respective ones of the first characteristic curves and relating temperature and the property of the fluid, and determining which of the first characteristic curves applies to the fluid, thus defining one of the second characteristic curves enabling determination of the fluid property from the second characteristic curve.

4. The method related in claim 1, wherein the step of determining the fluid property comprises storing a temperature coefficient relating temperature and fluid sonic propagation velocity in a memory, relating the sonic propagation velocity to a standard temperature and from the sonic propagation velocity at the standard temperature, obtaining the fluid property.

5. The method recited in claim 4, wherein the step of obtaining comprises obtaining the fluid property at the standard temperature and relating the property at the standard temperature to the temperature of the fluid.

6. The method recited in claim 1, wherein the step of determining the time comprises starting a counter upon propagating the sonic energy into the fluid and stopping the counter upon receipt of the sonic energy at the reception site.

7. The method recited in claim 1, further comprising determining the identity of the fluid from the relationship between sonic propagation velocity in the fluid and temperature.

8. Apparatus for determining a property of a fluid in a container, the property comprising the density or viscosity of the fluid, the apparatus comprising:
   means for propagating from a transmitter sonic energy into said fluid in the container;
   means for receiving the sonic energy at a reception site after a defined time delay determined by the nature of the fluid in the container;
   means for determining the time for the sonic energy to propagate from the transmitter to the reception site;
   means for determining the sonic propagation velocity of the sonic energy in the fluid from the determined time and from knowledge of the distance from the transmitter to reception site;
   means for determining the temperature of the fluid in the container; and
   means for determining the fluid property from the relationship between the sonic propagation velocity in the fluid and temperature.

9. The apparatus recited in claim 8, wherein the means for determining further comprises means for determining the pressure of the fluid in the container.

10. The apparatus recited in claim 8, wherein the means for determining the fluid property comprises look-up table memory means for storing a plurality of first characteristic curves relating temperature and fluid sonic propagation velocity and a plurality of second characteristic curves each associated with respective ones of the first characteristic curves and relating temperature and the property of the fluid, and means for determining which of the first characteristic curves applies to the fluid, thus defining one of the second characteristic curves, and means for determining the fluid property from the second characteristic curve.

11. The apparatus related in claim 8, wherein the means for determining the fluid property comprises means for storing a temperature coefficient relating temperature and fluid sonic propagation velocity, means for relating the sonic propagation velocity to a standard temperature and for obtaining the fluid property from the sonic propagation velocity at the standard temperature.

12. The apparatus recited in claim 11, wherein the means for obtaining comprises means for obtaining the fluid property at the standard temperature and for relating the property at the standard temperature to the temperature of the fluid.

13. The apparatus recited in claim 8, wherein the means for determining the time comprises a counter and means for starting the counter upon propagating the sonic energy into the fluid and stopping the counter upon receipt of the sonic energy at the reception site.

14. The apparatus recited in claim 8, further comprising means for determining the identity of the fluid from the relationship between sonic propagation velocity in the fluid and temperature.

* * * * *